United States Patent [19]

Van Overloop

[11] Patent Number: 4,540,412
[45] Date of Patent: Sep. 10, 1985

[54] DEVICE FOR MOIST HEAT THERAPY
[75] Inventor: Ronald R. Van Overloop, Palatine, Ill.
[73] Assignee: The Kendall Company, Boston, Mass.
[21] Appl. No.: 513,573
[22] Filed: Jul. 14, 1983
[51] Int. Cl.³ .................................. A61H 33/00
[52] U.S. Cl. ............................ 604/291; 604/305; 604/307; 128/399; 128/400
[58] Field of Search .......... 128/399, 400, 403; 604/291, 305, 307

[56] References Cited
U.S. PATENT DOCUMENTS

| | | | |
|---|---|---|---|
| 2,095,651 | 10/1937 | Ronzi | 128/397 |
| 2,379,657 | 7/1945 | Ryberg | 604/307 |
| 2,736,317 | 2/1956 | Alexander | 604/291 X |
| 3,089,492 | 5/1963 | Owens | 604/305 |
| 3,867,939 | 2/1975 | Moore et al. | 128/400 X |
| 3,929,131 | 12/1975 | Hardwick | 128/403 X |
| 4,376,437 | 3/1983 | Sundheim et al. | 604/291 X |

*Primary Examiner*—Edward M. Coven
*Attorney, Agent, or Firm*—Powell L. Sprunger

[57] ABSTRACT

A device for patient therapy in the use of wet dressings comprising, a device for generating heated moist air, and a sheet of substantially air impervious material to cover the wet dressing. Spaced portions of the sheet are secured to the patient. The generating device is coupled to the inside of the sheet intermediate the sheet and the patient to permit passage of the heated moist air onto the wet dressing.

11 Claims, 7 Drawing Figures

U.S. Patent  Sep. 10, 1985  4,540,412
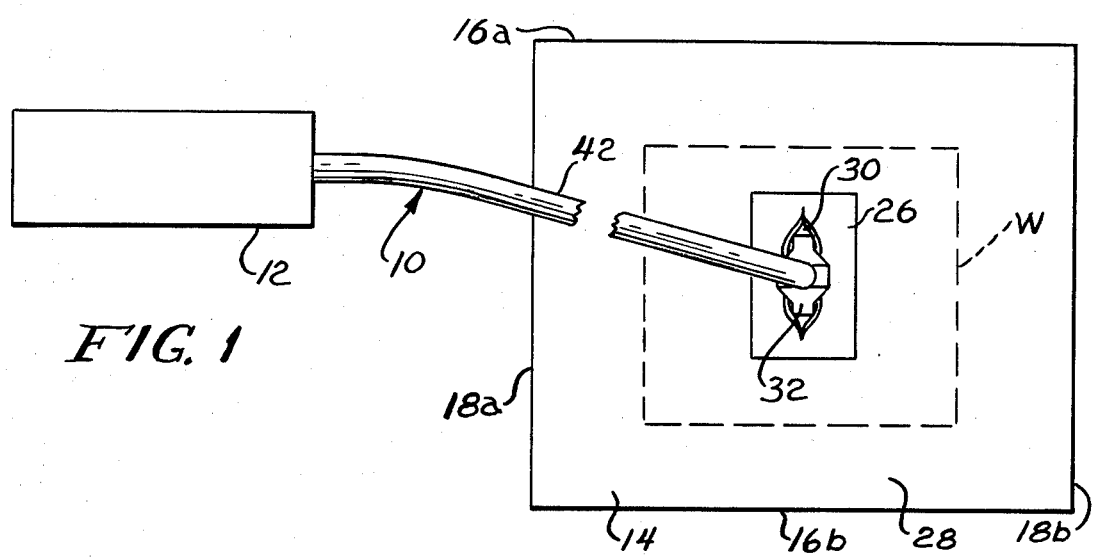
FIG. 1
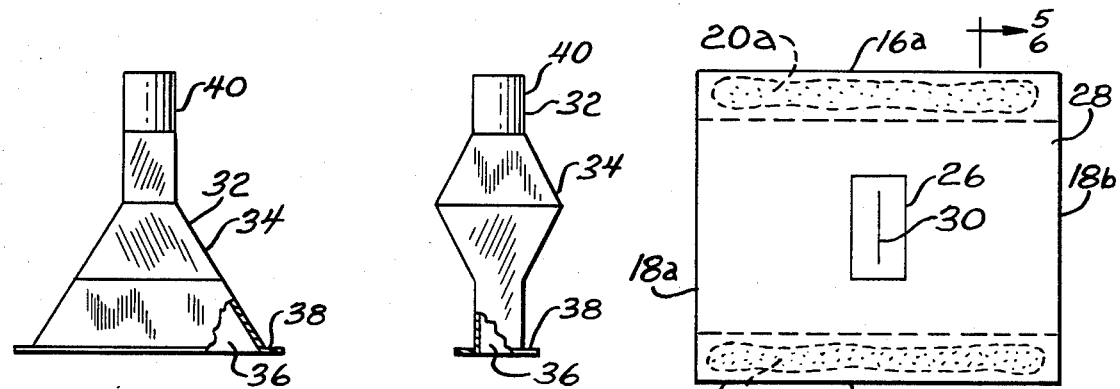
FIG. 2   FIG. 3   FIG. 4
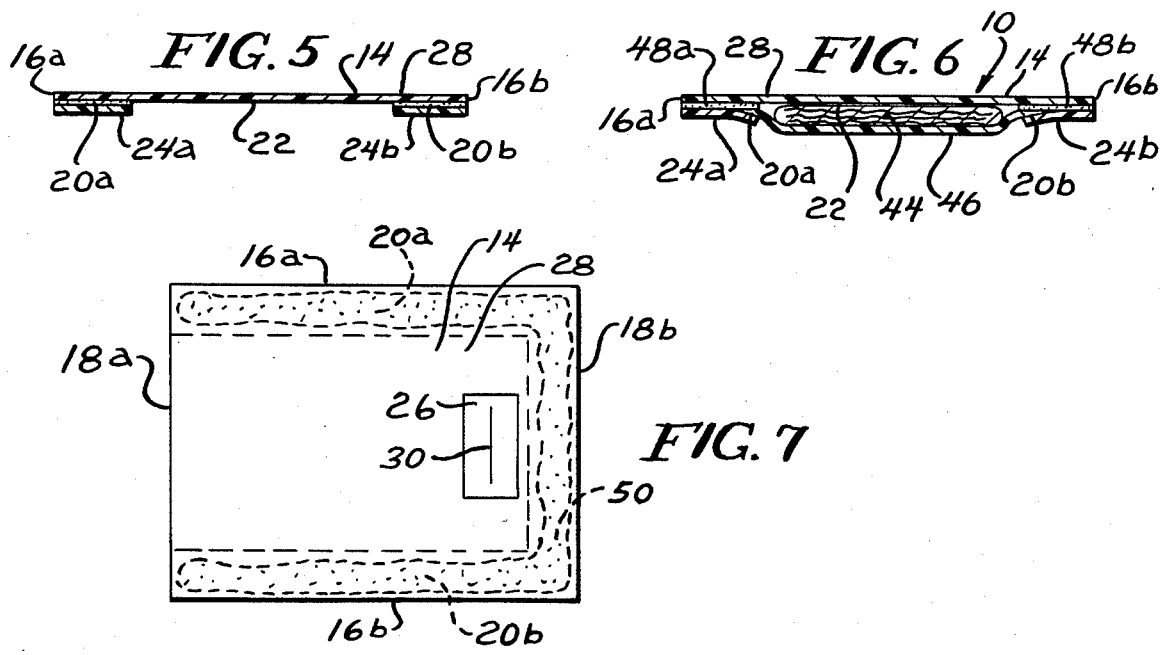
FIG. 5   FIG. 6
FIG. 7

DEVICE FOR MOIST HEAT THERAPY

BACKGROUND OF THE INVENTION

The present invention relates to devices for patient therapy, and more particularly to devices in the use of wet dressings.

In the past, wet dressings have been heated and used in moist heat therapy for a number of patient afflictions. Prior wet dressings normally comprise a foil package which retains a multi-ply gauze sheet impregnated with a sterile liquid. The packages are heated in a suitable manner for a period of time, such as beneath a heat lamp, after which the gauze is removed from the package and applied in heated form to the patient. The conditions for which heated wet dressings may be used in moist heat therapy include the following: (a) localized tissue infections, such as boils, carbuncles, eye inflammation, lymphangitis, and phlebitis; (b) ulcerations, such as decubitus ulcers, skin ulcers, and venous ulcers; (c) surgical wounds, such as infected suture wounds, hemorrhoidectomy, and pilonidal cysts; (d) traumatized tissue, such as lacerations, contusions, and accidental amputations; and (e) dermatological conditions, such as contact dermatitis, and psoriasis. Generally, the longer the wet dressing retains its heat and moisture, the better it serves its purpose.

SUMMARY OF THE INVENTION

A principal feature of the present invention is the provision of an improved device for patient therapy in the use of wet dressings.

The device comprises means for generating heated moist air, a sheet of substantially air impervious material to cover the wet dressing, and means for securing spaced portions of the sheet to the patient. The device has means for coupling the generating means to the inside of the sheet intermediate the sheet and the patient.

A feature of the present invention is that the heated moist air passes from the generating means beneath the sheet onto the wet dressing.

Another feature of the invention is that the device maintains the wet dressing in a heated condition for an extended period of time.

Yet another feature of the invention is that the device maintains the wet dressing in a moist condition for an extended period of time.

Further features will become more fully apparent in the following description of the embodiments of this invention and from the appended claims.

DESCRIPTION OF THE DRAWINGS

In the drawings:

FIG. 1 is a fragmentary plan view of a device for patient therapy of the present invention;

FIG. 2 is a front elevational view, partly broken away, of a coupler for the device of FIG. 1;

FIG. 3 is a side elevational view, partly broken away, of the coupler of FIG. 2;

FIG. 4 is a top plan view of one embodiment of a sheet for the device of FIG. 1;

FIG. 5 is a sectional view taken substantially as indicated along the line 5—5 of FIG. 4;

FIG. 6 is a fragmentary sectional view taken substantially as indicated along the line 6—6 of FIG. 4; and FIG. 7 is a top plan view of another embodiment of a sheet for the device of FIG. 1.

DESCRIPTION OF THE PREFERRED EMBODIMENTS

Referring now to FIGS. 1-5, there is shown a device generally designated 10 for patient therapy in the use of wet dressings W on a patient's skin. The device 10 has a humidifier-heater 12 which generates heated and moist air by heating the air and introducing moisture into the air, and a sheet 14 of substantially air impervious flexible material, such as polyurethane.

The sheet 14 has a pair of opposed side edges 16a and 16b, and a pair of opposed end edges 18a and 18b connecting the side edges 16a and b. The sheet 14 has an adhesive 20a and 20b on a lower surface 22 of the sheet 14 and extending along the side edges 16a and b. The sheet 14 may have a pair of release sheets 24a and 24b covering the adhesive 20a and b. The sheet 14 has a reinforcement 26, such as a piece of adhesive tape, on an upper surface 28 of the sheet 14, and a slit 30 extending through the reinforcement 26 and sheet 14, with the reinforcement 26 surrounding the slit 30.

The device 10 has a hollow coupler 32 which may be made from a suitable plastic material. The coupler 32 has a wall 34 defining an elongated narrow lower port 36, and the coupler 32 has an outwardly directed flange 38 extending peripherally around the port 36 at a lower end of the coupler 32. The coupler 32 also has an upper tubular section 40, and the device 10 has an elongated conduit 42 which communicates between the humidifier-heater 12 and the tubular section 40 of the coupler 32.

In use, a wet dressing W is initially heated in its moistened state, and is placed on the skin of the patient. Next, the release sheets 24a and b are removed from the adhesive 20a and b to expose the adhesive 20a and b, and the sheet 14 is placed over the wet dressing W with the adhesive 20a and b securing opposed sides of the sheet 14 to the patient's skin. The lower end of the coupler 32 is inserted through the slit 30, with the flange 38 retaining the coupler 32 in place in the sheet 14. Next, the humidifier-heater 12 is energized, and the humidifier-heater 12 heats and moistens air. The heated moist air passes from the humidifier-heater 12 through the conduit 42 and coupler 32 beneath the sheet 14 onto the wet dressing W. Thus, the heated and moist air maintains the wet dressing W in a heated and moist condition for an extended period of time, and excess air beneath the sheet 14 passes through the free ends of the sheet 14 adjacent the end edges 18a and b of the sheet 14.

Another embodiment of the present invention is illustrated in FIG. 6, in which like reference numerals designate like parts. In this embodiment, the device 10 also has a sheet 14 of flexible substantially air impervious material, such as polyurethane. In this embodiment, the wet dressing comprises a pad 44 beneath the sheet 14 to retain moisture. The pad 44 may comprise a polypropylene needle punched filler material, or a gauze material. The device 10 has a fluid pervious layer 46 beneath the pad 44 with sides of the layer 46 being secured to sides of the sheet 14 in order to secure the pad 44 in place beneath the sheet 14. The layer 46 may have adhesive 48a and b adjacent opposed sides of the layer 46 in order to secure the layer 46, pad 44, and sheet 14 to the patient's skin. Of course, the device 10 may have release sheets 24a and b covering the adhesive 48a and b prior to use of the pad 44.

In use, the heated and moist air is passed beneath the sheet 14 and onto the pad 44 in order to maintain the pad 44 in a heated and moist condition for an extended period of time. In other respects, the layer 46, pad 44, and sheet 14 of FIG. 6 operates in a manner as previously described with the sheet 14 and wet dressing W of FIGS. 1-5.

Another embodiment of the present invention is illustrated in FIG. 7, in which like reference numerals designate like parts. In this embodiment, the sheet 14 has an adhesive 20a and b on the lower surface of the sheet 14 and extending along the side edges 16a and b. Also, in this embodiment, the sheet 14 has an adhesive 50 on the lower surface of the sheet 14 and extending along one end edge 18b, with the slit 30 being located adjacent the end edge 18b.

In use, the heated and moist air is passed through the slit 30 onto a wet dressing beneath the sheet 14 in order to maintain the wet dressing in a heated and moist condition, and excess air passes longitudinally along the sheet and out from beneath the sheet at the other end adjacent the end edge 18a. Of course, the sheet 14 of FIG. 7 may be constructed with a pad and layer in order to form an integral wet dressing, as previously described in connection with FIG. 6.

The foregoing detailed description is given for clearness of understanding only, and no unnecessary limitations should be understood therefrom, as modifications will be obvious to those skilled in the art.

I claim:

1. A device for patient therapy comprising:
    a preheated wet dressing comprising a gauze impregnated with a sterile liquid;
    means for generating a continuous supply of treating fluid comprising heated moist air;
    a sheet of substantially air impervious material to cover the wet dressing, said sheet having a pair of opposed side edges, a pair of opposed end edges connecting the side edges, and means defining an opening in the sheet;
    means for securing spaced portions of the sheet to the patient comprising adhesive on the lower surfaces of the sheet adjacent opposed edges of the sheet;
    means for coupling the generating means to the inside of the sheet opening intermediate the sheet and the patient to permit passage of the heated moist air onto the wet dressing, the coupling means including a coupler with a lower, outwardly directed flange located inside of the sheet opening and a conduit communicating between the generating means and the coupler; and
    means for permitting said treating fluid to flow outwardly between the sheet and a patient comprising at least one edge of the sheet being free of attachment to the patient whereby, in use of the device, a barrierless opening is defined between the at least one free edge of the sheet and the patient.

2. The device of claim 1 wherein the coupler is received in a slit of the sheet defining the opening.

3. The device of claim 2 including a reinforcement secured to the sheet and extending around the opening, said reinforcement having a slit aligned with the sheet slit.

4. The device of claim 1 wherein the coupler has a wall defining an elongated narrow port.

5. The device of claim 1 wherein the sheet comprises polyurethane film.

6. The device of claim 1 wherein the wet dressing comprises a pad to retain moisture, said pad being retained beneath the sheet.

7. The device of claim 6 wherein the pad comprises a polypropylene needle punched filler material.

8. The device of claim 6 including a layer of fluid pervious material beneath the pad.

9. The device of claim 8 wherein the layer is secured to the sheet.

10. The device of claim 1 wherein said adhesive is on the lower surfaces of the sheet adjacent opposed side edges of the sheet, and further comprising adhesive on the lower surface of the sheet adjacent one of the end edges of the sheet and extending therealong, the other end edge defining said one free edge of the sheet.

11. The device of claim 10 wherein the generating means is coupled to the sheet adjacent the one end edge.

* * * * *